United States Patent [19]

Yamao et al.

[11] Patent Number: 4,931,387

[45] Date of Patent: Jun. 5, 1990

[54] ANALYSIS IMPLEMENT HAVING AN OXYGEN SUPPLYING LAYER

[75] Inventors: Yasuo Yamao, Kyoto; Shigeru Fujioka, Shiga, both of Japan

[73] Assignee: Kabushiki Kaisha Kyoto Daiichi Kagaku, Japan

[21] Appl. No.: 714,185

[22] Filed: Mar. 20, 1985

[30] Foreign Application Priority Data

Mar. 30, 1984 [JP] Japan ................................. 59-64211

[51] Int. Cl.[5] .............................................. C12Q 1/26
[52] U.S. Cl. ........................................ 435/25; 435/4; 435/805
[58] Field of Search .................. 435/4, 25, 28, 189, 435/818, 817, 805; 436/807, 904

[56] References Cited

U.S. PATENT DOCUMENTS

| | | | |
|---|---|---|---|
| 3,983,005 | 9/1976 | Goodhue et al. | 435/805 |
| 4,318,985 | 3/1982 | Bauer et al. | 435/28 |
| 4,484,987 | 11/1984 | Gough | 435/817 |
| 4,604,264 | 8/1986 | Rothe et al. | 435/805 |

FOREIGN PATENT DOCUMENTS 0137521  4/1985  European Pat. Off. ............... 435/4

*Primary Examiner*—Robert J. Warden
*Assistant Examiner*—Janelle Graeter
*Attorney, Agent, or Firm*—Darby & Darby

[57] ABSTRACT

Disclosed is an analysis implement including a support and a reagent layer containing an oxidase applied to the support such that one surface of the reagent layer is exposed to an air atmosphere. A hydrophobic, porous, oxygen permeable layer is positioned between the reagent layer and the support, such that oxygen can permeate to the layer containing oxidase.

1 Claim, 2 Drawing Sheets

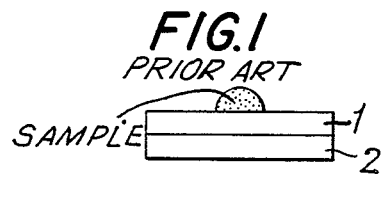
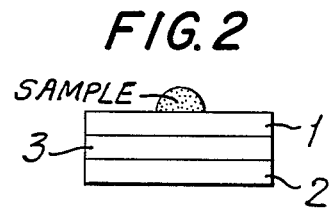
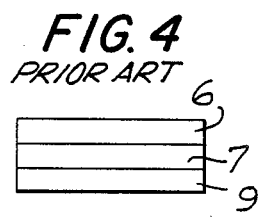
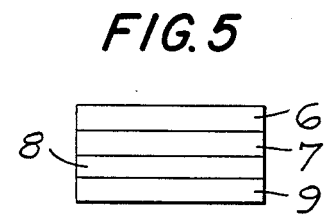
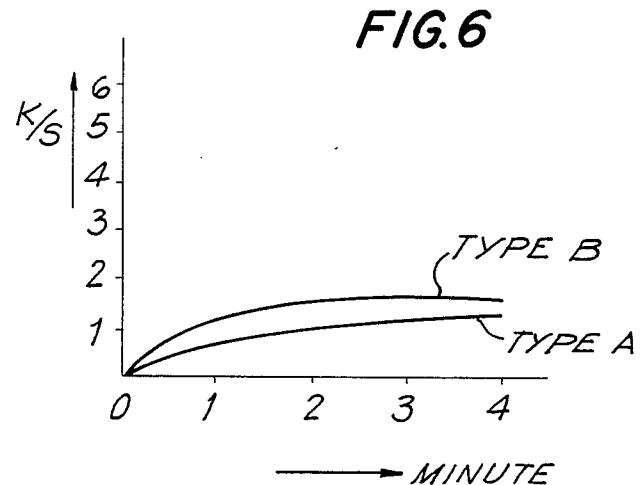

ANALYSIS IMPLEMENT HAVING AN OXYGEN SUPPLYING LAYER

BACKGROUND OF THE INVENTION

This invention relates to an implement containing oxidase, for analyzing body fluids, particularly body fluid components.

Analysis by enzyme reaction is suitable for the analysis of liquid samples because it provides specific detection under mild conditions. The oxidase reaction is widely used. With these methods, a sample material or its reaction product is oxidized by an oxidase. The hydrogen peroxide produced thereby, is reacted with a peroxidase to form a coloring matter, and the coloring matter is determined by colorimetry. Other detecting means such as fluorimetry, emission spectroscopy, and various types of electrodes are also available.

Well known methods of colorimetric analysis of hydrogen peroxide include the method using "Trinder's reagent" (Ann, Clin, Biochem, Vol. 6, page 24, 1969) and using an oxidizable chromogen such as o-anisidine, benzidine, o-tolidine, and tetramethylbenzidine. In these methods, hydrogen peroxide produced by the action of an oxidase is reacted with a peroxidase, is coupled with aminoantipyrine and a phenol by oxidation. The resultant coloring material is determined. Alternatively, the oxidizable chromogen is directly oxidized to form coloring material. This system has an advantage that the same detection means can be used with different types of oxidases. Thus, its application to various analysis items is being widely investigated. Oxidases essential to clinical examination includes glucose oxidase, urecase, cholesterol oxidase, glyco-3-phosphoric acid oxidase, choline oxidase, acyl-CoA-oxidase, sarcosine oxidase, various amino acid oxidases, bilirubin oxidase, lactose oxidase, pyruvic acid oxidase, galactose oxidase, and glycerol oxidase.

Heretofore, a solution containing one such oxidase, peroxidase, and a chromogen has been used for body fluid analysis in clinical examination.

Alternatively, reagents comprising the above analysis composition integrally mixed and dried (hereinafter called "solid reagent") have been widely used to answer the fundamental requirements of quick and simple analysis.

For example, a test film of plastic film applied with a detection system of a dispersion of this oxidase and peroxidase in polymer has been disclosed in U.S. Pat. No. 3,630,957. U.S. Pat. No. 3,992,158 describes a multi-layer test film comprising a liquid permeable and light transmittable substrate provided thereon with a reagent layer and developing layer. Modified multi-layer test film, include those which have an added a barrier layer as in U.S. Pat. No. 4,066,403 specification, with a registration layer and radiation blocking layer as in U.S. Pat. No. 4,144,306; and with a migration blocking layer as in U.S. Pat. No. 4,166,093. Most of these embodiments of solid reagent contain oxidase.

Deficient oxygen supply in these methods using oxidases can cause errors in measurements due to a reduced degree of coloring.

The oxygen requirement for oxidation in a solid reagent is furnished by dissolved oxygen present in the solid reagent and atmospheric oxygen dissolved in the reaction system.

However, as is obvious from the theoretical base shown below, sufficient reaction is not to be expected from the dissolved oxygen in the sample alone.

Solubility of air in pure water is 0.0167 ml/ml at 25° C. under 1 atm. of which oxygen is 0.0057 ml/ml. (Chemical Handbook compiled by Chemical Society of Japan, Basic Chapter II, page 621, 1965, Maruzen). The dissolved oxygen 0.0057 ml/ml is calculated as 25 $\mu$mol/dl, but because of other substances also dissolved in the sample, the actual quantity of oxygen is less than 25 $\mu$mol/dl.

Components of normal blood serum include, for example, glucose 360–580 $\mu$mol/dl, cholesterol 360–670 $\mu$mol/dl, triglyceride 34–152 $\mu$mol/dl, and uric acid 12–42 $\mu$mol/dl. In abnormal cases, these values increase. Since the above solid reagent is generally applied to the sample undiluted or diluted several times at most, it is obvious that the dissolved oxygen in the sample alone cannot completely oxidize the substrate.

Therefore, should only the dissolved oxygen be used, sufficient oxidation will be impossible when the concentration of the sample is higher than the normal range, even for a substance of very low concentration such as uric acid in serum or even when the concentration is in normal range for other substances in serum.

Oxidase in the above mentioned multi-layer test film is contained in the reagent layer between the sample developing layer and support layer, and deficiency of oxygen is remarkable.

The time required for the quantity of oxygen, decreased through consumption, to recover to the specified level is much longer than the reaction time, since the oxygen is supplied to the solid reagent only after it is dissolved into the liquid sample drop from the atmosphere. This is fatal to expediting and simplifying the process.

Even the test film described in U.S. Pat. No. 3,603,957, comprising only a reagent layer formed on a substrate body, has as a drawback that the single reagent layer cannot exhibit its effect of direct contact of its surface with air, since the sample dropped on the reagent layer form a liquid intermediate layer between the reagent layer and air. Thus, only the dissolved oxygen in the reaction system present before the reaction and a small quantity of oxygen absorbed through the part of the reaction longer but not covered by the sample are used for the oxidation reaction.

In other words, even in the case of single reagent layer, oxygen required by the oxidase reaction is not fully supplied, leading to inaccurate analysis.

Japanese Laid Open Patent Specification No. 57-208,997 discloses a multi-layer test film containing the oxidase in the outmost porous developing layer to solve the drawback of deficient oxygen. The porous nature of the oxidase-containing layer provides a larger area of contact with atmospheric oxygen. This type of test film provides a larger effect relative to an analysis implement having only a reagent layer on the support.

Even with this test film, the quantity of oxygen is still not sufficient, and it has been ascertained by the present inventors that the problem still remains, particularly for a sample containing a high concentration of the compound in question.

SUMMARY OF THE INVENTION

As a result of earnest investigation of the structure of solid reagent in consideration of such circumstances, the present inventors have found that the above problem can be solved by the provision of a clearance between the reagent layer and the support so that the reagent layer is brought in contact with air from the support side.

OBJECTS OF THE INVENTION

It is an object of the present invention to provide an analysis implement which permits quick and accurate determination of an analysis requiring oxygen by furnishing oxygen to the reagent layer also from the support side.

Another object of the invention is to provide an analysis implement which permits sufficient oxidation in the determination of samples of particularly high concentration to accurately determine sample levels.

The porous hydrophobic oxygen layer according to the invention attains the above objects by supplying oxygen also from the underside of the reaction system, containing air in advance and being able to circulate it.

BRIEF DESCRIPTION OF THE DRAWINGS

FIG. 1 is a schematic side view illustrating an example of the conventional analysis implement.

FIG. 2 is a schematic side view illustrating an embodiment of the analysis implement according to the invention.

FIG. 3 is a schematic side view showing another embodiment of the analysis implement according to the invention.

FIG. 4 is a schematic side view showing an example of a prior-art analysis imlement.

FIG. 5 is a schematic side view illustrating still another embodiment of the analysis implement of the invention.

FIGS. 6, 7, and 8 are diagrams showing the reaction time courses obtained using each embodiment of the analysis implement of the invention.

DETAILED DESCRIPTION OF THE INVENTION

Figure 7:
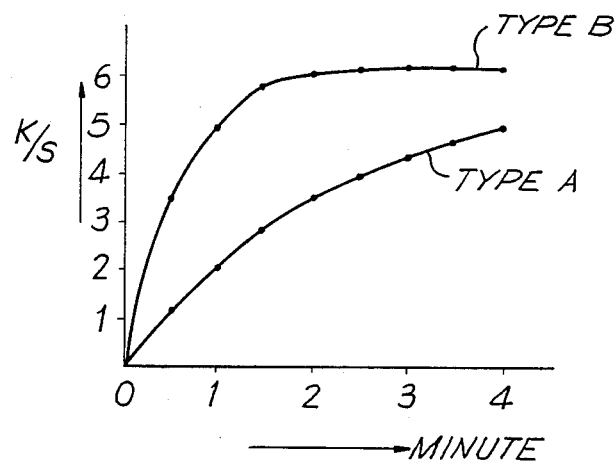

The analysis implement according to the invention will now be detailed with reference to the drawings.

FIG. 1 shows an analysis implement which is simply made of a support applied with a mixture of a reagent and a binder of film-forming polymer and dried, in which 1 represents the reagent layer and 2 is the support. FIG. 2 shows an embodiment of the analysis implement according to the invention. It is made of a support as shown in FIG. 1 stuck with a porous hydrophobic material (oxygen permeable layer 3) and over which is applied a reagent, and dried. The reagent layers in FIGS. 1 and 2 contain oxidase, a hydrogen peroxide detecting reagent, etc.

When the sample is dropped on these analysis implements, it forms a droplet on each implement. In one or two minutes, the conventional analysis implement shown in FIG. 1 starts to develop color around the droplet and the coloring proceeds slowly toward the center of the droplet area. Ultimately, however, the center, of the droplet area does not attain to the expected intensity of coloration. The analysis implement shown in FIG. 2, on the other hand, starts uniform color development in the whole area attached with the droplet and finally the coloring becomes complete with expected intensity. This phenomenon is due to the fact that the quantity of oxygen dissolved in the sample is insufficient to effect oxidation and the droplet interferes with the dissolution of oxygen into the reaction system.

In other words, in the area of droplet periphery in FIG. 1, the reaction system is in direct contact with air and the reaction fully proceeds. In the center area on the other hand the reaction is incomplete. In the analysis implement in FIG. 2, oxidation proceeds uniformly owing to the oxygen permeable layer provided.

In the practical examination, the sample is removed after an adequate reaction time (1-2 min) from sample dropping, and the condition of color development is observed by naked eye or instrument. Therefore, the analysis implement in FIG. 1 gives inaccurate results based on an uneven, low reaction rate, while the analysis implement in FIG. 2 gives satisfactory results.

FIG. 3 shows another embodiment of the analysis implement of the invention, in which the support also serves as an oxygen supplier. Such combined use of substrate and oxygen supplier simplifies the manufacture of the implement and reduces the cost.

FIG. 4 shows the fundamental structure of the unified multi-layer analysis implement by the inventors disclosed in Laid Open Patent Specification No. 58-122690. It comprises integratedly a light reflective support 9, a reagent layer 7 containing a reagent which produces an optically detectable change by reacting with the aimed component and is dissolved or forms a zol by the solvent of the sample system, and a detection layer 6 which transfers the received liquid sample to the reagent layer and uniformly diffuses the optically detectable material produced or reduced in the reagent layer. FIG. 5 shows an analysis implement provided with an oxygen supply layer 8 between the reagent layer 7 and substrate body 9 shown in FIG. 4. These unified multi-layer analysis implements can be used for measuring various items. Here, the effect of the oxygen supply layer is demonstrated using the embodiments which contain an oxidase and hydrogen peroxide detecting reagent in the reagent layers. When the sample is dropped on the unified multi-layer analysis implements in FIG. 4 and FIG. 5, it reaches the reagent layers as somewhat spreading in the detection layers and spreads laterally in the interface between the detection layers and the reagent layers and dissolves the reagent layers. The sample which has dissolved the reagent layers diffuses into the detection layers while reacting with the reagent, and the mixed reaction solution containing all the compositions of the reagent layers is transferred into the detection layers. Uniform color development was observed in either case, but the unified multi-layer analysis implement in FIG. 5 showed faster reaction and more intense coloring than that in FIG. 4. This difference in color developing rate is due to the fact that the unified multi-layer analysis implement in FIG. 4 is in contact with air only on one side (opposite to the substrate) of the reaction system, while that in FIG. 5 contacts air on both sides of the reaction system, securing very smooth supply of air to the reaction system.

The oxygen permeable layer of the invention has a porous hydrophobic structure made of a material subjected to hydrophobic treatment, such as nonwoven fabric, woven fabric, paper, metal mesh, nylon mesh, and porous ceramics. When the substrate also serves as an oxygen supplier, it is made of various resins such as polyester, acrylic, nylon, polystyrene, polyurethane, metacrylic, phenol, molded into porous structure, or porous hydrophobic materials such as cement, ceramics, glass filter. The oxygen permeable layer can also be formed of a hydrophobic polymer which is a solid at room temperature. Such a layer is formed in the following manner: The polymer is dissolved in an organic solvent and dispersed therein is another solvent which is insoluble in the organic solvent and has a higher boiling point than the organic solvent to form an emulsion. This emulsion is applied on the support and both solvents are evaporated. Such hydrophobic polymers are exemplified by cellulose acetate, ethyl cellulose, polyvinyl butyral, polystyrene, polyurethane, polyester, acrylic, nylon, polyphenol, polymethacrilic, polyvinyl acetate, nitro-cellulose, and low polymer of polyamino acid.

To further illustrate the oxygen permeable layer of the invention, but not by way of limitation, the following Examples are given.

EXAMPLE 1

Two types of film were prepared; a single white polyester film 0.125 mm thick (made by Toray Industries, Inc.) and the same white polyester film laminated thereon with a porous hydrophobic film oxygen supply layer (made by Sekisui Chemical Co., Ltd.; trade mark "Cellopore", made of polyethylene 150 μm thick) using double-coated tape. Coated thereon was a coating solution of the composition given below in a thickness of 0.2 mm and dried to form a reagent layer which develops color in accordance with the quantity of glucose present. These films were cut into 10 mm × 10 mm pieces, and 50 μm of the sample of 90 mg/dl (500 μmol/dl) aqueous glucose solution was dropped in the center of each piece. The dropped sample partly soaked into the reagent layer, but the greater part formed a droplet on the surface of the reagent layer. The piece having reagent layer directly on the polyester film (hereinafter designated as type A) started slowly to develop color from the periphery of the droplet area, and at the end of reaction the center was also colored but the periphery was much more deeply colored than the center. The piece having reagent layer on the porous film (hereinafter designated as type B) started color development in the whole droplet area and was uniformly colored at the end of reaction. The reaction rate was also larger in type B.

| (Composition of coating solution for reagent layer formation for type A and type B) | |
|---|---|
| Cellulose acetate | 8.0 g |
| 1,2-dichloroethane | 70 ml |
| Glucose oxidase | 200 mg |
| Peroxidase | 200 mg |
| Polyvinyl pyrrolidone (K-90) | 150 mg |
| 4-aminoantipyrine | 12 mg |
| 1,7-dihydroxynaphthalene | 70 mg |
| Ethanol | 8.0 ml |
| 0.1M phosphoric acid buffer solution (pH 7.5) | 16 ml |

EXAMPLE 2

A coating solution of the composition given below was applied on the white polyester film of Example 1 in a thickness of 0.2 mm and dried to form a porous hydrophobic structure (type C). With this analysis implement (type C), the same experiment as described in Example 1 was performed. The type C gave nearly equal uniformity of color development as type B, but the developing rate was somewhat slower than that of type B. In the case of type C, the oxygen permeable layer was ascertained to have the characteristics of an oxygen permeable layer, because the film does not allow the coating solution for forming reagent layer to permeate completely.

| (Composition of coating solution for forming oxygen permeable layer) | |
|---|---|
| Polyvinyl butryal resin (Polymerization degree: 700) | 5 g |
| Acetone | 50 ml |
| Purified water | 10 ml |
| Surface active agent (Tween 20) | 500 mg |

EXAMPLE 3

Instead of the white polyester film in Example 1, a ceramics plate subjected to surface hydrophobic treatment was used. An analysis implement (type D) having a substrate combined with oxygen permeable layer was obtained by applying the coating solution of. The resultant implement gave the uniformity, intensity, and rate of color development similar to type B.

EXAMPLE 4

To examine the effect of oxygen supply layer of the invention, the reaction time course of type A and type B implements prepared in Example 1 was determined to examine the effect of the oxygen permeable layer of the present invention. Reflectance at 550 nm measured by a reflectometer (integrating-sphere 220 A spectrophotometer for reflectance measurement made by Hitachi, Ltd.) on color-developed serum a and serum b of known glucose concentration.

The measuring procedure was as follows:

(1) Drop each of serum a (glucose concentration: 82 mg/dl. 456 μmol/dl) and serum b (glucose concentration: 320 mg/dl, 1778 μmol/dl) on the type A and type B analysis implements to start reaction. Use reaction time during which the sample is on the analysis implement was varied from 0 to 4 minutes in 30-sec increments.

(2) When each reaction time is reached, surplus sample was wiped with absorbent cotton (oxidation is nearly ended upon the removal of surplus sample), and after one minute, the reflectance was measured to determine the aspect of oxidation.

The K/S value is calculated from the reflectance obtained by the following equation:

$$K/S = (1-R)^2/(2 \times R)$$

where K is a constant, S is the dissipation coefficient of a specified reflection medium, and R is reflectance. The variation with time of the K/S value (time course of oxidation reaction) on serum a is shown in FIG. 6 and that on serum b is shown in FIG. 7.

This relationship is a simplified Kubelka-Munk equation (refer to "Reflectance Spectroscopy" by Gustav-Kortum, page 106-111, Springer-Verlas, 1969) and the K/S value is linearly proportional to the mol concentration.

As is obvious from FIGS. 6 and 7, in an analysis implement having an oxygen permeable layer, the reaction proceeds quickly reaching the end point in 2-3 mins., while in an analysis implement having no oxygen permeable layer, the reaction rate is slower and it is impossible to attain quick, accurate determination.

EXAMPLE 5

Two types of film were prepared; a single white polyester film 0.125 mm thick (made by Toray Industries, Inc.), and the same white polyester film laminated thereon with an oxygen permeable membrane filter layer (made by Sumitomo Electric Industries, Ltd.) using double-coated tape. Applied to the film was a coating solution for triglyceride of the composition given below uniformly in a thickness of 0.2 mm and width of 20 mm, and dried at 4° C. for 2 hours to form a reagent layer. Then, the surface of the reagent layer was lightly moistened and cotton broadcloth 2 cm wide (made by Toyobo Co., Ltd). was pressure bonded thereon to form a detecting layer. These films were cut into halves of the reagent layer in the coating direction and then into 5-mm width at right angles to coating direction. Thus, unified multi-layer analysis implements for glyceride measurement comprising a 5 mm × 10 mm detecting layer and reagent layer and unified multi-layer analysis implements having an oxygen permeable layer in addition were obtained.

| (Composition of coating solution for reagent layer formation for type E and type F) | |
| --- | --- |
| Lipoprotain lipase | 300 mg |
| Glycerol kinase | 50 mg |
| Glycero triphosphate oxidase | 100 mg |
| Peroxidase | 100 mg |
| Adenosinetriphosphate | 600 mg |
| 4-aminoantipyrine | 350 mg |
| Sodium salt of 3,5-dimenthoxy-N-ethyl-(2-hydroxy-3-sulfopropyl) aniline | 375 mg |
| Magnesium chloride | 0.2 mg |
| Sodium alginate | 1600 mg |
| 0.2M phosphoric acid buffer solution (pH 8.0) | 100 ml |

On the unified multi-layer analysis implement formed of a reagent layer directly applied to white polyester film (hereinafter designated as type E) and on that having a reagent layer formed on a membrane filter (hereinafter designated as type F), 10 μl of serum C (triglyceride concentration: 157 mg/dl 1768 μmol/dl was dropped. Reaction curves obtained are shown in FIG. 8.

Figure 8:
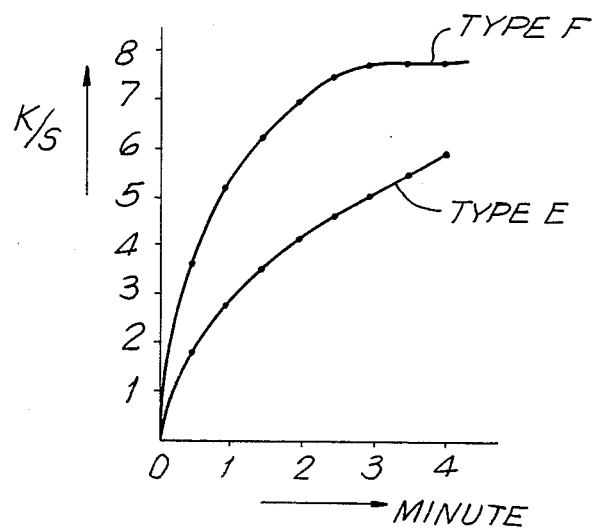

FIG. 8 shows that type F has faster reaction rate than type E and proves the remarkable effect of the oxygen permeable layer that makes oxygen available on both surfaces of the reagent layer.

Preferred Examples have been described above, but it is to be understood that various changes can be made without departing from the spirit of the invention.

Preferable porous hydrophobic materials available as the oxygen permeable layer are hydrophobic porous film, hydrophobic nonwoven fabric and woven fabric, hydrophobic paper, metal mesh and nylon mesh, porous resin, ceramics subjected to surface hydrophobic treatment, porous glass, and porous metal film. It is also possible to use a porous hydrophilic material rendered hydrophobic on one side and combined with the reagent layer on this side. Also, any porous material can be used if it is not completely permeated by the coating solution for forming the reagent layer.

The support (2) can also serve as a oxygen supply layer, if it is porous and hydrophobic.

As detailed above, the analysis implement having an oxygen permeable layer according to the invention provides smooth progress of oxidation since it permits oxygen required for oxidation of solid reagent in the reaction system to permeable from the support side. Thus, an analysis implement having a solid reagent containing oxidase that permits quick and accurate analysis is obtained.

What is claimed is:
1. An analysis implement, comprising:
   a support;
   a reagent layer containing an oxidase applied to said support such that one surface of said reagent layer is exposed to an air atmosphere; and
   a hydrophobic, porous, oxygen permeable layer positioned between said reagent layer and said support, such that oxygen can permeate to said layer containing oxidase from both surfaces of said layer containing oxidase.

* * * * *